United States Patent [19]

Bors et al.

[11] Patent Number: 4,960,924

[45] Date of Patent: Oct. 2, 1990

[54] MERCAPTOALKYL ACETOACETATES

[75] Inventors: Daniel A. Bors, Warminster; William D. Emmons, Huntingdon Valley, both of Pa.

[73] Assignee: Rohm and Haas Company, Philadelphia, Pa.

[21] Appl. No.: 265,185

[22] Filed: Oct. 31, 1988

[51] Int. Cl.$^5$ .......................................... C07C 149/20
[52] U.S. Cl. ................................. 560/178; 526/216; 526/224
[58] Field of Search ......................................... 560/178

[56] References Cited

U.S. PATENT DOCUMENTS 3,542,855  11/1970  Maschel .............................. 560/178
3,689,568   9/1972  Eletts et al. ........................... 568/73

OTHER PUBLICATIONS

L. W. C. Miles and L. N. Owen, J. Chemical Society, 817–826 (1952).
M. F. Carroll and A. R. Bader, J. Am. Chem. Soc., vol. 75, 5400–5402 (1953).
R. J. Clemens and J. A. Hyatt, J. Organic Chem., vol. 50, 2431–2435 (1985).

*Primary Examiner*—Vivian Garner

[57] ABSTRACT

This invention relates to mercaptoalkyl acetoacetates and a process for preparing mercaptoalkyl acetoacetates. The process embraces the reaction of TKD (a diketene-acetone adduct) with hydroxy-functional mercaptans. Preferred is the reaction of TKD with 2-mercaptoethanol to yield mercaptoethyl acetoacetate. Mercaptoethyl acetoacetate is an effective chain transfer agent in free radical polymerization reactions with the benefit of introducing reactive acetoacetate functionally into the formed polymer.

2 Claims, No Drawings

MERCAPTOALKYL ACETOACETATES

FIELD OF THE INVENTION

This invention relates to mercaptoalkyl acetoacetates and a process for the preparation of mercaptoalkyl acetoacetates. The process encompasses the reaction of TKD, a diketene-acetone adduct, namely, 2,2,6-trimethyl-1,3-dioxen-4-one, with hydroxy-functional mercaptans. The process produces superior yields of the pure mercaptoalkyl acetoacetates relative to the corresponding reaction with diketene.

More particularly, this invention relates to mercaptoalkyl acetoacetates which are effective chain transfer agents in free-radical polymerization reactions. The mercaptoalkyl acetoacetates function as chain transfer agents and thereby introduce reactive acetoacetate functional endgroups into at least some of the polymer molecules so prepared.

DESCRIPTION OF THE PRIOR ART

Miles and Owen (L. W. C. Miles and L. N. Owen, J. Chem. Soc., 817–826 (1952)) disclose a process for preparing 2-mercaptoethyl acetate by direct acetylation of 2-mercaptoethanol with acetic anhydride.

It has long been known that aliphatic, cycloaliphatic, or aromatic compounds containing hydroxyl groups can react with diketene to produce acetoacetic esters. The catalytic use of acid-base couples as acetic acid and tertiary aliphatic amines was disclosed in U.S. Pat. No. 2,351,366.

The reaction of diketene with hydroxyl groups is also disclosed in U.S. Pat. No. 3,542,855. The process for the preparation of acetoacetic esters by reacting diketene with a mono-, di-, or tri-hydric aliphatic alcohol having 1 to 18 carbon atoms in the presence of certain levels of certain tertiary diamines is disclosed.

Carroll and Bader (M. F. Carroll and A. R. Bader, J. Am. Chem. Soc., Vol. 75, 5400–5402(1953)) disclose the acidcatalyzed reactions of diketene with ketones which yielded 2,2-disubstituted-4-methyl-6-keto-1,3-dioxenes, many reactions of which dioxenes paralleled those of diketene. The adduct of diketene with acetone yielded 2,2,6-trimethyl-1,3-dioxen-4-one (TKD); the reactions of TKD with methanol or 1-butanol to yield methyl acetoacetate or n-butyl acetoacetate are exemplified.

Clemens and Hyatt (R. J. Clemens and J. A. Hyatt, J. Org. Chem., Vol.50, 2431–2435(1985)) disclose some of the deficiencies of acetoacetylation of nucleophiles with diketene, a highly reactive, lacrymatory, and toxic reagent. They disclose rapid acetoacetylation of a series of aliphatic alcohols with TKD which proceeded with excellent yield and provided product of excellent purity. They further disclose that thiophenol and two aliphatic mercaptans are acetoacetylated in good yield (using TKD). They also allege that "this acetoacetylation process (using TKD and mercaptan) is probably the method of choice for preparing thioacetoacetate esters". However, they exemplify the reaction of TKD with thiophenol to yield a 72% yield of thiophenyl acetoacetate, not the thioacetoacetate discussed in the reference, such as, for example, hydroxyphenyl thioacetoacetate. The teaching of the Clemens and Hyatt article with respect to formation of thioacetoacetates is incomplete and unclear. Further, this teaching is not resolved by our Comparative Example directed to this reaction.

U.S. Pat. No. 3,689,568 discloses a process for preparing primary mercaptans which comprises reacting hydrogen sulfide with certain alpha-olefins and a certain trivalent organic phosphorous initiator under certain conditions. Generically disclosed, but not exemplified or claimed as olefin reactants are vinyl esters. There is no suggestion, however, of vinyl acetoacetate as an alpha-olefin to be used in the process disclosed nor does the disclosure direct one to try a vinyl ester of a multifunctional carboxylic acid.

SUMMARY OF THE INVENTION

This invention relates to mercaptoalkyl acetoacetates and a process for the preparation of mercaptoalkyl acetoacetates. This invention also relates to the process of reacting mercaptoalkanols with a diketene-ketone adduct such as, for example, TKD, 2,2,6-trimethyl-1,3-dioxen-4-one, at a temperature at least high enough to cause the decomposition of the diketene-ketone adduct in order to produce high yields of mercaptoalkyl acetoacetates.

This invention also relates to mercaptoalkyl acetoacetates which function as chain transfer agents in free radical polymerization reactions. With the primary chain transfer reaction involving the mercapto group of the mercaptoalkyl acetoacetates, at least some of the polymer chains produced in the free radical polymerization reaction contain acetoacetate functionality incorporated into the formed polymer.

DETAILED DESCRIPTION OF THE INVENTION

This invention is directed to a new class of compounds, mercaptoalkyl acetoacetates of the Formula

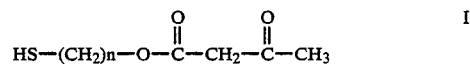

wherein n is 1 to 8. Preferably, the C atom of the $(CH_2)_n$ radical adjacent to the O atom is unsubstituted. More preferably, n in the Formula I is from 1 to 3. Most preferably n in the Formula I is 2.

This invention is also directed to a process for the preparation of the mercaptoalkyl acetoacetates of Formula I. The process comprises contacting a mercaptoalkanol with TKD at a temperature sufficient to cause decomposition of TKD. A temperature in the range of from about 80° C. to about 170° C. will normally be employed. In the preferred enmbodiment of this invention temperatures of from about 110° C. to about 130° C. are employed.

This invention is also directed to the use of mercaptoalkyl acetoacetates of the Formula I as chain transfer agents in free radical addition polymerization reactions. These reactions embrace the preparation of oligomers and polymers by the free radical polymerization of ethylenically unsaturated monomers in solution in substantially aqueous media or in organic solvent media; in bulk; or in emulsion, dispersion or suspension form in substantially aqueous media, as, for example, in aqueous latex preparation, or in organic solvent media, as, for example, in non-aqueous dispersion preparation.

The following examples are intended to illustrate the subject compounds and the process for preparing the subject compounds to which this invention is directed. They are not intended to limit the invention as other applications of the invention will be obvious to those of ordinary skill in the art.

Example 1: Preparation of mercaptoethylacetoacetate

In a 300 ml. round bottom flask fitted with a thermometer, mechanical stirrer, Dean Stark trap and reflux condenser was placed 25.0g.(0.32 mole) of 2-mercaptoethanol. This was stirred and heated to 130° C.; 45.4g. (0.32 mole) of 2,2,6-trimethyl-1,3-dioxen-4-one (TKD) was added dropwise at a uniform rate over the period of one hour. Heating was continued for ½ hour; acetone distillate was collected in the Dean Stark trap. After distillate collection was completed, the mixture was distilled under vacuum and the portion boiling at 110°–115° C.(at 5 mm. Hg.) was collected to give a colorless liquid of mercaptoethylacetoacetate. The yield was about 90% based on starting material. The product was identified by NMR spectroscopy.

Example 2: Preparation of 3-mercapto-2-butylacetoacetate

The reaction of TKD with 3-mercapto-2-butanol was carried out according to the process of Example 1. The yield of the acetoacetate functional mercaptan was about 80%.

Comparative Example: Preparation of 4-hydroxyphenylthioacetoacetate or 4-mercaptophenyl acetoacetate In a 500 ml. round bottom flask equipped with a nitrogen sparge, mechanical stirrer, condenser with Dean-Stark trap, and thermometer was placed 50.0g. (0.4 mole) hydroxythiophenol and 56.3g. TKD. The mixture was heated to 130° C. and acetone was collected in the trap. Heating was continued for two hours. The reaction mixture was analyzed by NMR; no starting material was present and little to none of either reaction product was found.

Example 4: Use of mercaptoethylacetoacetate as a chain transfer agent

In a 500ml. round bottom flask equipped with a thermometer, nitrogen sparge, mechanical stirrer and reflux condenser was placed 60.0g. of xylene. This was heated to 105° C. with stirring. Two monomer solutions were separately premixed. The first contained 42.5g. of butyl methacrylate, 7.5g. of methyl methacrylate, and 9.2g. of mercaptoethylacetoacetate. The second mixture contained 42.5g. of butyl methacrylate, 7.5g. of methyl methacrylate, and 1.1g. of t-butyl peroctoate. The two solutions were pumped simultaneously into the xylene solution over a period of 0.8 hour. After 0.3 hr. of additional heating, in additional 0.2g. of t-butyl peroctoate was added and heating was continued for 0.5 hr. The heat was removed. The polymer solution was at 60.54% solids content. Gel permeation chromatography molecular weights were $\overline{Mw}=3730$ and $\overline{Mn}=1770$, demonstrating the efficacy of the mercaptoethylacetoacetate as a chain transfer agent to those of ordinary skill in the art.

What is claimed is:

1. A compound of the formula

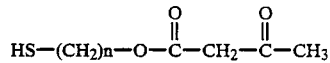

wherein n is 1 to 8.

2. The compound of claim 1 wherein n is 1 to 3.